(12) United States Patent
Lin (10) Patent No.: US 10,925,884 B2
(45) Date of Patent: Feb. 23, 2021

(54) METHODS OF DIAGNOSING AND TREATING HEPATOCELLULAR CARCINOMA

(71) Applicant: MacKay Memorial Hospital, Taipei (TW)

(72) Inventor: Jiunn-Chang Lin, Taipei (TW)

(73) Assignee: MACKAY MEMORIAL HOSPITAL, Taipei (TW)

( * ) Notice: Subject to any disclaimer, the term of this patent is extended or adjusted under 35 U.S.C. 154(b) by 411 days.

(21) Appl. No.: 15/953,526

(22) Filed: Apr. 16, 2018

(65) Prior Publication Data

US 2018/0296575 A1     Oct. 18, 2018

Related U.S. Application Data

(60) Provisional application No. 62/486,014, filed on Apr. 17, 2017.

(51) Int. Cl.
*A61K 31/58*      (2006.01)
*C12Q 1/6886*    (2018.01)
*G01N 33/574*    (2006.01)

(52) U.S. Cl.
CPC ............ *A61K 31/58* (2013.01); *C12Q 1/6886* (2013.01); *C12Q 2600/118* (2013.01); *C12Q 2600/158* (2013.01); *G01N 33/57438* (2013.01); *G01N 2333/904* (2013.01)

(58) Field of Classification Search
CPC ............ A61K 31/58; G01N 33/57438; G01N 2333/904
See application file for complete search history.

(56) References Cited

PUBLICATIONS

Williams et al. Br. J. Cancer, 1993, vol. 68, pp. 1210-1215 (Year: 1993).*
Beardwell et al. Cancer Chemother. Pharmacol., 1983, vol. 10, pp. 158-160 (Year: 1983).*
Zhu et al. Journal of Clinical Oncology, Jun. 20, 2009, vol. 27, No. 18, pp. 3027-3025 (Year: 2009).*
Faivre et al. Clin. Cancer Res., 2011, vol. 17, No. 13, pp. 4504-4512 (Year: 2011).*
Montgomery et al. Cancer Res., 2008, vol. 68, No. 11, pp. 4447-4454 (Year: 2008).*
Li et al. BMC Veterinary Research (2015) 11:123, 8 pages (Year: 2015).*

* cited by examiner

*Primary Examiner* — James D. Anderson (57) ABSTRACT

Disclosed herein is a novel use of HSD3B1 in disease diagnosis. According to embodiments of the present disclosure, the mRNA or protein level of HSD3B1 may serve as an indicator for diagnosing hepatocellular carcinoma. Also disclosed herein are methods for treating hepatocellular carcinoma by use of HSD3B1 inhibitor.

12 Claims, 5 Drawing Sheets

METHODS OF DIAGNOSING AND TREATING HEPATOCELLULAR CARCINOMA

CROSS-REFERENCE TO RELATED APPLICATIONS

This application relates to and claims the benefit of U.S. Provisional Application No. 62/486,014, filed Apr. 17, 2017; the content of the application is incorporated herein by reference in its entirety.

BACKGROUND OF THE INVENTION

1. Field of the Invention

The present disclosure in general relates to the field of cancer diagnosis and treatment. More particularly, the present disclosure relates to methods of diagnosing hepatocellular carcinoma (HCC) via determining the expression level of 3-beta-hydroxysteroid dehydrogenase type 1 (HSD3B1), and methods of treating HCC by use of HSD3B1 inhibitors.

2. Description of Related Art

Hepatocellular carcinoma (HCC) is the most common primary liver malignancy and is a leading cause of cancer-related death worldwide. HCC occurs predominantly in patients having chronic liver diseases (e.g., chronic inflammation caused by hepatitis B or C virus infection, fatty liver diseases, cystic liver fibrosis, and etc.) and/or cirrhosis. According to the reports, the vast majority of HCC occurs in Asia and sub-Saharan Africa, where hepatitis B virus infection is endemic and many patients are infected from birth. The incidence of HCC in the United States and other developing countries is increasing due to an increase in hepatitis C virus infections. It is more common in males than females, in which the ratio between males and females is about 2.4:1.

As with other cancers, early diagnosis plays a key role in the treatment outcome. Since the vast majority of HCC occurs in people with chronic liver diseases and/or cirrhosis, liver screening is commonly advocated in this population. Several imaging modalities, including ultrasonography (US), computed tomography (CT), magnetic resonance imaging (MRI), positron emission tomography (PET) and angiography, are employed as diagnostic tools for HCC. In addition to imaging techniques, the diagnosis of HCC can be made by biomarkers; for example, alpha-fetoprotein (AFP), immunoglobulin M (IgM) immunocomplexes, and autoantibodies. However, potential drawbacks that may be encountered when employing these diagnostic methods include, increased radiation, low-resolution, high-cost, low-sensitivity and/or low-accuracy.

Regarding the treatment, multiple treatment options are available for HCC, including curative resection, liver transplantation, radiotherapy, and chemotherapy. Unfortunately, most of these treatments cannot produce a satisfactory effect on HCC patients due to the limitations of, for instance, transplant rejection, infection complications, low-specificity, low-efficiency, and/or adverse side-effect.

In view of the foregoing, there exists in the related art a need for novel methods for efficiently diagnosing and treating HCC in a subject in need thereof.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a method of determining whether a subject has or is at risk of developing hepatocellular carcinoma. The present method comprises, (a) obtaining a sample from the subject;
(b) measuring the mRNA or protein level of 3-beta-hydroxysteroid dehydrogenase type 1 (HSD3B1; mRNA reference sequence: NM_000862.2; protein reference sequence: NP_000853) in the sample; and
(c) determining whether the subject has or is at risk of developing hepatocellular carcinoma based on the mRNA or protein level of HSD3B1 measured in step (b).

According to some embodiments of the present disclosure, when the mRNA or protein level of HSD3B1 in the sample is higher than that of a healthy subject, then the subject has or is at risk of developing hepatocellular carcinoma.

The sample assessed by the present method is preferably a liver tissue.

The second aspect of the present disclosure pertains to a method of treating a subject in need thereof; for example, the subject having HCC. The method comprises administering to the subject an effective amount of an inhibitor of HSD3B1.

Optionally, the method further comprises identifying the subject having HCC by the method described in the first aspect of the present disclosure prior to the administration of HSD3B1 inhibitor. Specifically, the sample (e.g., a liver tissue) is first obtained from the subject (e.g., the subject suspected of having HCC) followed by being subject to a quantification assay, in which when the expression level (either the mRNA level or the protein level) of HSD3B1 in the sample is higher than that of a healthy subject, then the subject has HCC. Based on the quantification results, the HSD3B1 inhibitor is then administered to the subject having HCC.

Non-limiting examples of HSD3B1 inhibitor include, trilostane, epostane, cyanoketone, dutasteride and sunitinib. According to the working example of the present disclosure, the HSD3B1 inhibitor is trilostane.

The effective amount administered to the subject is about 0.01-100 mg/kg body weigh per day; preferably, about 0.1-10 mg/kg body weight per day; more preferably, about 1-5 mg/kg body weight per day.

The subject assessable and/or treatable with the method in accordance with any aspect and embodiments mentioned in the present disclosure is a mammal; preferably, a human.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "administered", "administering" or "administration" are used interchangeably herein to refer a mode of delivery, including, without limitation, orally, intravenously, intratumorally, intramuscularly, intraperitoneally, intraarterially, intracranially, or subcutaneously administering an agent (e.g., the HSD3B1 inhibitor).

As used herein, the term "treat," "treating" and "treatment" are interchangeable, and encompasses partially or completely preventing, ameliorating, mitigating and/or managing a symptom, a secondary disorder or a condition associated with HCC. The term "treating" as used herein refers to application or administration of one or more active agents to a subject, who has a symptom, a secondary disorder or a condition associated with HCC, with the purpose to partially or completely alleviate, ameliorate, relieve, delay onset of, inhibit progression of, reduce severity of, and/or reduce incidence of one or more symptoms, secondary disorders or features associated with HCC. Symptoms, secondary disorders, and/or conditions associated with HCC include, but are not limited to, abdominal pain, fatigue, anorexia, cachexia, ascites, and biliary obstruction. Treatment may be administered to a subject who exhibits only early signs of such symptoms, disorder, and/or condition for the purpose of decreasing the risk of developing the symptoms, secondary disorders, and/or conditions associated with HCC.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the HSD3B1 inhibitor), such as molar concentration, mass concentration, volume concentration, molality, mole fraction, mass fraction and mixing ratio.

As used herein, the term "inhibitor" refers to a substrate that blocks or suppresses the activity of an enzyme (e.g., HSD3B1), for example, reducing, eliminating, masking and/or preventing the physiological and/or pathological expression, action, activity and/or function of the enzyme. However, The term "inhibitor" does not imply that each and every one of these expression, action, activity and function must be inhibited at the same time. The term "inhibitor" includes reversible, irreversible, competitive and noncompetitive inhibitors. According to the preferred examples of the present disclosure, the inhibit or HSD3B1 is an antagonist of HSD3B1.

The term "patient" and "subject" are used interchangeably herein, and refer to a mammal including the human species that may be assessed and/or treated by the methods of the present invention. The term "subject" is intended to refer to both the male and female gender unless one gender is specifically indicated.

The term "healthy subject" refers to a subject that does not have a disease (e.g., the subject does not have HCC). For example, a healthy subject has not been diagnosed as having a disease and is not presenting with two or more (e.g., two, three, four or five) symptoms associated with the disease.

II. Description of the Invention

The present disclosure is based, at least in part, on the discovery that HSD3B1 is overexpressed in HCC, and is associated with cell growth and migration. Accordingly, the present disclosure provides a method of marking a diagnosis of HCC via evaluating the expression level of HSD3B1. Based on the tumor-promoting activity of HSD3B1, also disclosed herein are methods of treating HCC by use of HSD3B1 inhibitors.

(i) Diagnosis of HCC by Evaluating the Expression of HSD3B1

The first aspect of the present disclosure is directed to a method of determining whether a subject has or is at risk of developing HCC. The present method comprises obtaining a sample from the subject; measuring the mRNA or protein level of HSD3B1 in the sample; and determining whether the subject has or is at risk of developing HCC based on the mRNA or protein level of HSD3B1 measured.

According to embodiments of the present disclosure, when the mRNA or protein level of HSD3B1 in the sample is higher than that of a healthy subject, then the subject has or is at risk of developing HCC. In contrast, when the mRNA or protein level of HSD3B1 in the sample is equal to or lower than that of a healthy subject, then the subject does not have or is not at risk of developing HCC.

The measured value may be expressed in either relative amount or absolute amount. The mRNA or protein level of HSD3B1 in the sample may be measured by any assay commonly used or known by persons skilled in the art. For example, the protein level of HSD3B1 can be measured by western blot analysis, enzyme-linked immunosorbent assay (ELISA), immunohistochemistry (IHC) assay, immunocytochemistry (ICC) assay, immunofluorescence (IF) assay, or luminex assay. According to one specific example, the protein level of HSD3B1 is measured by western blot analysis.

For the purposes of measuring the mRNA level, total RNA is first extracted from the sample by a chemical solution with high corrosiveness (e.g., phenol, trichloroacetic acid/acetone, and Trizol) followed by neutralization with chloroform. After centrifugation, the aqueous phase that contains the RNA sample is precipitated by an organic solution, such as ethanol and isopropanol. The RNA sample is then washed with ethanol to remove the contaminated protein followed by drying (e.g., air dry and vacuum dry) to obtain the RNA pellet. Then, the RNA pellet is dissolved in diethylpyrocarbonate-treated $H_2O$ (DEPC $H_2O$), and converted into the corresponding cDNA by reverse transcription (RT). In general, RT is performed by mixing the RNA with primer Oligo(dT)$_{20}$, deoxy-ribonucleoside triphosphate (dNTP, which comprises dATP, dGTP, dTTP, and dCTP), reverse transcriptase, reaction buffer, and optionally, the co-factor of reverse transcriptase (e.g., $MgCl_2$). Preferably, the reaction mixture further comprises dithiothreitol (DTT), a redox reagent used to stabilize the reverse transcriptase, and RNase inhibitor preventing the degradation of RNA during RT. The cDNA serving as a template may then be quantified by quantitative polymerase chain reaction assay (qPCR) or microarray (e.g., cDNA array and oligonucleotide array).

Since the cancer cells may migrate/infiltrate from the primary lesion (e.g., liver) through the blood system to the secondary lesion, the sample assessed by the present method may be any type of tissue in the subject. For example, the sample may be a suspension of cells, such as whole blood, serum, plasma or urine. Alternatively, the sample may be a solid tissue, for example, liver, lung, kidney, spleen, thymus, brain and pancreas. According to the working example of the present disclosure, the sample is a liver tissue.

Based on the quantification result, a physician or a clinical practitioner may administer to a subject in need thereof (i.e., the subject having HCC) a suitable therapeutic regimen in time.

(ii) Treatment of HCC by Use of HSD3B1 Inhibitor

The second aspect of the present disclosure is directed to a method of treating HCC in a subject. The method comprises administering to the subject an effective amount of an HSD3B1 inhibitor.

Optionally, the subject having HCC is first identified by the present diagnostic method described in Part (i) of the present specification. Specifically, the sample is first obtained from the subject suspected of having HCC. Depending on desired purposes, the expression level (either the mRNA expression level or the protein expression level) of HSD3B1 in the sample may be measured by any quantification assay mentioned above. Whether the subject has HCC is then determined based on the expression level of HSD3B1, in which when the expression level of HSD3B1 in the sample is higher than that of a healthy subject, then the subject has HCC. Alternatively, the HCC may be identified by other diagnostic assays, for example, US, CT, MRI, PET or angiography.

The HSD3B1 inhibitor may be a compound exhibiting inhibitory effect on the expression, activity and/or function of HSD3B1. Non-limiting examples of the compound exhibiting inhibitory effect on HSD3B1 include, trilostane, epostane, cyanoketone, dutasteride and sunitinib. Alternatively, the HSD3B1 inhibitor may be a nucleic acid, which specifically targets the mRNA and down-regulates the expression of HSD3B1; such a nucleic acid may be provided in the form of a small interference ribonucleic acid (siRNA), a small hairpin ribonucleic acid (shRNA), a micro-ribonucleic acids (miRNA), or a DNA sequence corresponding thereto. According to preferred examples of the present disclosure, the HSD3B1 inhibitor is trilostane.

According to some embodiments of the present disclosure, the subject is a mouse. In these embodiments, the HSD3B1 inhibitor is administered to the subject in an amount of 0.125-1,250 mg/kg body weigh per day; preferably, 1.25-125 mg/kg body weigh per day; more preferably, 1.25-25 mg/kg body weigh per day. According to one specific example, the HSD3B1 inhibitor is administered in an amount of 30 mg/kg body weigh per day. According to an alternative example, the HSD3B1 inhibitor is administered in an amount of 60 mg/kg body weigh per day.

A skilled artisan may readily determine the human equivalent dose (HED) of the HSD3B1 inhibitor, based on the doses determined from animal studies provided in working examples of this application. According to some embodiments the amount of the HSD3B1 inhibitor suitable for use in a human subject may be in the range of about 0.01-100 mg/Kg/day, such as 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg/kg body weight per day for human; preferably, 0.1-10 mg/kg body weigh per day; more preferably, 1-5 mg/kg body weigh per day. According to one specific example, the HED of HSD3B1 inhibitor is about 2-3 mg/kg body weigh per day. According to an alternative example, the HED of HSD3B1 inhibitor is about 4-5 mg/kg body weigh per day.

As would be appreciated, the dosing regimen may vary with specified factors, such as age, gender, bone mass, physiological condition, and other treatments (if any). For example, the HSD3B1 inhibitor may be administered to the subject 1-7 times per week (e.g., 1, 2, 3, 4, 5, 6 or 7 times per week) for 1, 2, 3, 4 or more consecutive weeks. Alternatively, the HSD3B1 inhibitor may be administered to the subject 1-10 times (e.g., 1, 2, 3, 4, 5, 6, 7, 8, 9 or 10 times) for every 2 weeks, every 3 weeks, every 4 weeks, every 5 weeks, every 6 weeks, every 7 weeks, every 8 weeks, every 9 weeks, or every 10 weeks; or once every month, every 2 months, or every 3 months, or longer. According to one working example of the present disclosure, the HSD3B1 inhibitor is administered to the subject daily for 18 consecutive days so as to produce the therapeutic effect.

According to embodiments of the present disclosure, the HSD3B1 inhibitor suppresses the proliferation and migration of HCC thereby suppressing the tumor growth in the subject.

As would be appreciated, the present method can be applied to the subject, alone or in combination with additional therapies that possess some beneficial effects to the subject in terms of HCC treatment. Depending on the intended purpose, the present method can be applied to the subject before, during, or after the administration of the additional therapies.

Optionally, the HSD3B1 inhibitor may be administered to the subject via any of the following routes, which include, but are not limited to, oral, enteral, transmucosal, and parenteral administration, in which the parenteral administration is any of subcutaneous, intradermal, intratumoral, intramuscular, intraarterial, intravenous, intraspinal, intrathecal or intraperitoneal injection.

According to the database of NCBI (National Center for Biotechnology Information, which is a part of the United States National Library of Medicine (NLM), a branch of the National Institutes of Health (NIH)), HSD3B1 has the protein reference sequence of NP_000853, which is encoded by gene HSD3B1 having the mRNA reference sequence of NM_000862.2.

As could be appreciated, in addition to HCC, the method illustrated in Part (I) or (II) of the present disclosure is useful in diagnosing or treating other cancers as long as HSD3B1 is overexpressed thereon.

In general, the subject suitable to be assessed and/or treated by the method in accordance with any aspect and embodiment of the present disclosure is a mammal; for example, for example, human, mouse, rat, guinea pig, hamster, monkey, swine, dog, cat, horse, sheep, goat, cow, and rabbit. Preferably, the subject is a human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

Patients

From August 2014 to May 2016, a total of 57 pairs of HCC and adjacent non-tumor liver tissues were collected from patients who underwent liver resection at the Department of Surgery of Mackay Memorial Hospital (MMH, Taiwan, R.O.C.). The samples were snap-frozen in liquid nitrogen for latter study. All human materials were obtained with informed consent and approved by the Institutional Review Board of Mackay Memorial Hospital.

Cell Culture and Reagents

Human HCC cancer cell lines (including Mahlavu, Hep3B, and Huh7) were cultured in Dulbecco's modified Eagle medium (DMEM), supplemented with 10% (v/v) fetal bovine serum and antibiotics (100 units/mL penicillin, 100 μg/mL streptomycin, and 2.5 μg/mL amphotericin B). All cell lines have been periodically authenticated by short tandem repeat analysis at Bioresource Collection and Research Center, Hsinchu, Taiwan (R.O.C.) and tested for being *mycoplasma* free. Trilostane was purchased from LKT Laboratories, St. Paul, Minn.

Colony Forming Assay

A total of 500 Mahlavu or Hep3B HCC cancer cells were seeded into 6-well plate and treated with various dosage of trilostane. The medium was replaced every 3 days. After 10 to 13 days, colonies were stained with 3% crystal violet and examined by microscopy. Colonies containing at least 50 individual cells were counted.

Wound Healing Assay

Mahlavu and Hep3B cells ($2\times10^5$ cells/well) were seeded into 6-well plates and grown to confluence overnight. A wound was made by scraping with a sterilized 200-μL pipette tip in the middle of the cell monolayer, and the cells were allowed to migrate to the denuded area for 24 hours. The percentage of wound closure was measured using Olympus IX71 light microscope (Olympus, Tokyo, Japan).

In Vivo Xenograft Model of HCC

All animal experiments were approved by the Institutional Animal Care and Use Committee of MacKay Memorial Hospital (Taiwan, R.O.C.). 6-week-old male BALB/c nude mice were injected subcutaneously with $1.0\times10^7$ Mahlavu cells into the bilateral back pad. When the tumor growth reached 50 mm$^3$, mice were randomly divided into three groups (n=5 mice each group): (1) low-dose group, in which 30 mg/kg of trilostane was intraperitoneally administered to the mouse every day for 18 days; (2) high-dose group, in which 60 mg/kg of trilostane was intraperitoneally administered to the mouse every day for 18 days; and (3) control group, in which vehicle control (Dimethyl sulfoxide, DMSO) of the same volume was intraperitoneally administered to the mouse every day for 18 days. The tumor volume was measured twice a week by the same investigator, and mice were sacrificed when tumors reached 10% of body weight.

Western Blot Analysis

Total cellular proteins were extracted, quantified, and subject to gel electrophoresis. Whole-cell lysates were isolated from Mahlavu cells. Equal amounts of proteins (40 µg/lane) were electrophoresed in 10% sodium dodecyl sulfatepolyacrylamide gel. The transferred membrane was blocked with 5% defatted milk and immunoblotted with primary antibodies against various proteins, including ERK (total form), p-ERK, p-AKT, E-cadherin, N-cadherin, Snail1, Twist, Vimentin, MLC II (total form), p-MLC II, ROCK, and GAPDH at room temperature for 3 hours. The antigen-antibody complexes were visualized with by chemiluminescence with the Amersham ECL detection system (GE Healthcare, Piscataway, N.J.).

Statistical Analysis

Statistical analysis was performed using the SPSS (version 13.0, Chicago, Ill.). Statistical analysis of independent experiments was carried out using two-tailed Student's t-test. Statistical significance was defined as $p<0.05$.

Example 1 Up-Regulation of HSD3B1 in HCC

For the purpose of identifying the expression level of HSD3B1 and HSD3B2 (mRNA reference sequence: NM_000198.3; protein reference sequence: NP_000189.1) in HCC, liver samples isolated from tumor (T) tissues and non-tumor (NT) tissues of HCC patients were respectively examined by western blot analysis. The results were illustrated in FIGS. 1A-1B and Table 1.

Based on the expression level, HCC patients were divided into two groups, in which in the patients of group I, the expression level of HSD3B1 or HSD3B2 was higher in the tumor tissues as compared to the non-tumor tissues (i.e., T>NT); by contrast, the expression level of HSD3B1 or HSD3B2 in the patient of group II was higher in the non-tumor tissues than in the tumor tissues (i.e., T<NT).

Figure 1A:
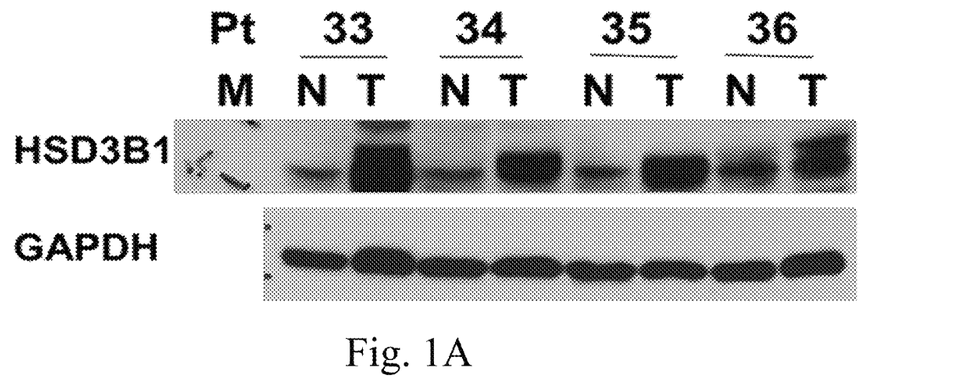
FIGS. 1A and 1B are the data respectively depicting the expression level of specified protein in tumor (T) and non-tumor (N) tissue (FIG. 1A) and in HCC patients (FIG. 1B) according to Example 1 of the present disclosure.
Figure 1B:
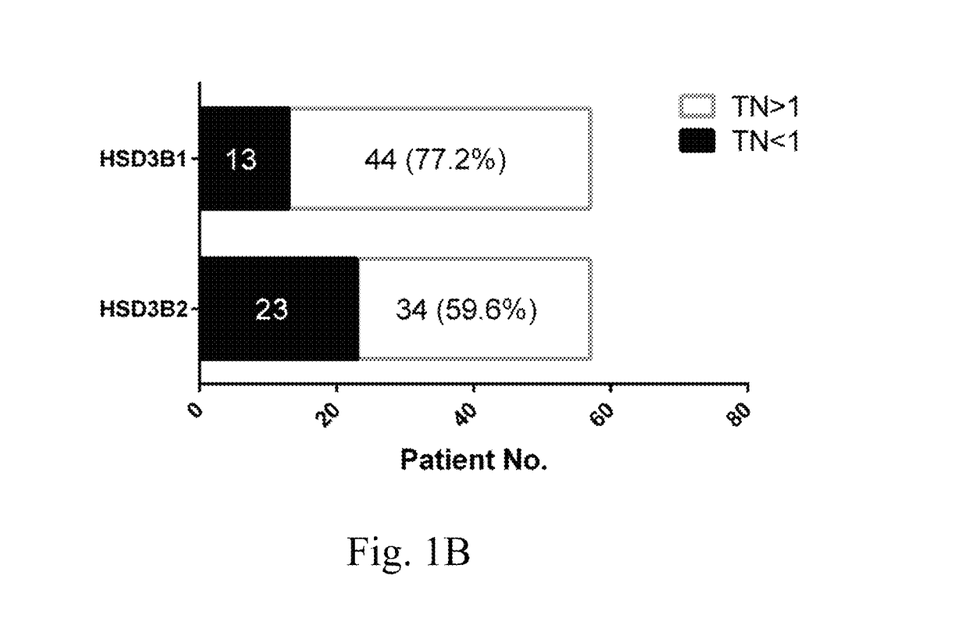

As the data of FIGS. 1A and 1B depicted, compared with non-tumor (NT) tissues, the expression level of HSD3B1 and HSD3B2 was up-regulated in HCC tumor tissues. Further, the patients of group I, who had higher expression of HSD3B1 in tumor tissues, had a significant lower percentage to be early stage according to the tumor, node, metastasis (TNM) staging system (Table 1).

TABLE 1

Clinical characteristics of 57 HCC patients

| characteristics | Group 1 (T > N, n = 44) | Group 2 (T < N, n = 13) | P value |
|---|---|---|---|
| Age (mean) | 58.8 +− 10.6 | 62.8 +− 10.3 | 0.23 |
| Gender, male | 29 (65.9%) | 9 (69.2%) | 0.26 |
| Hepatitis B | 24 | 7 | |
| Hepatitis C | 15 | 5 | |
| nonB nonC | 5 | 5 | 0.18 |
| AFP (median) | 21.7 | 10.2 | 0.33 |
| Tumor grade 3, 4 | 20 (47.6%) | 7 (53.9%) | 0.17 |
| Vascular invasion | 3 (6.8%) | 0 | 0.45 |
| TNM stage I | 29 (65.9%) | 12 (92.3%) | |
| stage II & III | 15 (34.1%) | 1 (7.7%) | 0.03 |

The data indicated that HSD3B1 was overexpressed in HCC tissues.

Example 2 HSD3B1 Antagonist Inhibits Cell Proliferation and Migration In Vitro

To investigate the effect of HSD3B1 on the development and process of HCC, Mahlavu and Hep3B cells were respectively treated with trilostane (an antagonist of HSD3B1) followed by the analysis of colony forming assay and wound healing assay. The results were respectively depicted in FIGS. 2A-2E.

Figure 2A:
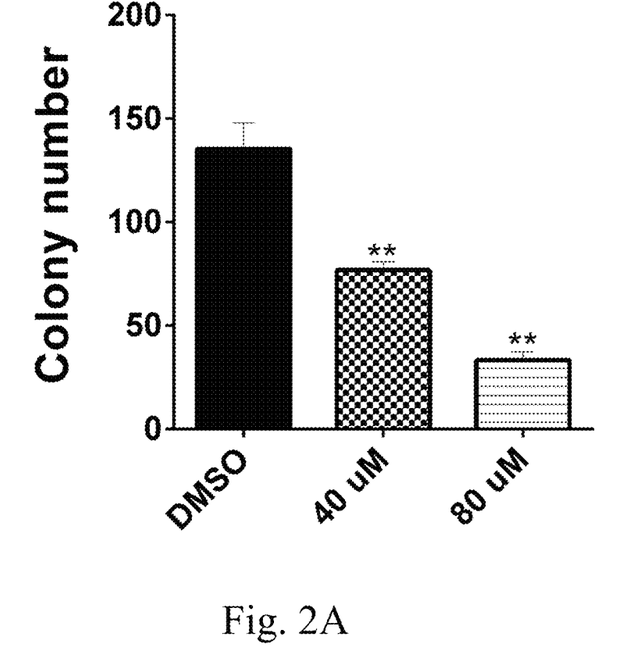
FIGS. 2A-2E are the data respectively depicting the inhibitory effect of trilostane on the proliferation and migration of mahlave cells (FIGS. 2A, 2C and 2E) and Hep3B cells (FIGS. 2B and 2D) according to Example 2 of the present disclosure.
Figure 2B:
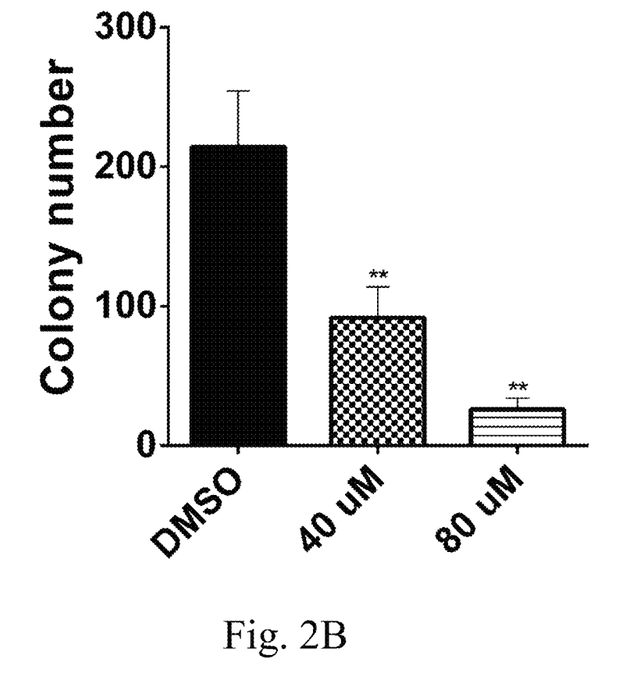
Figure 2C:
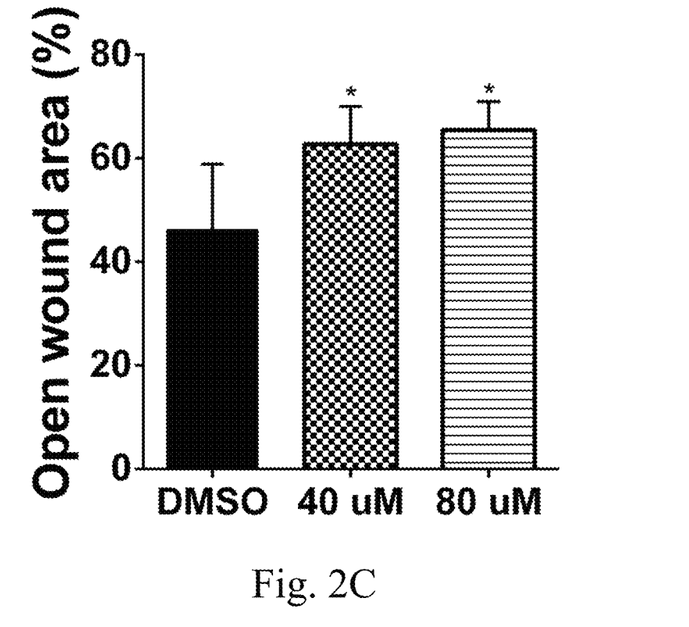
Figure 2D:
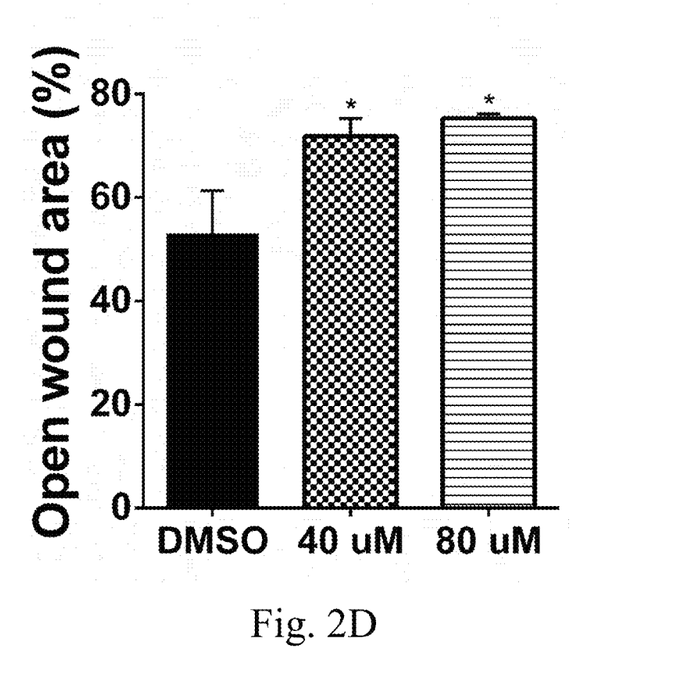
Figure 2E:
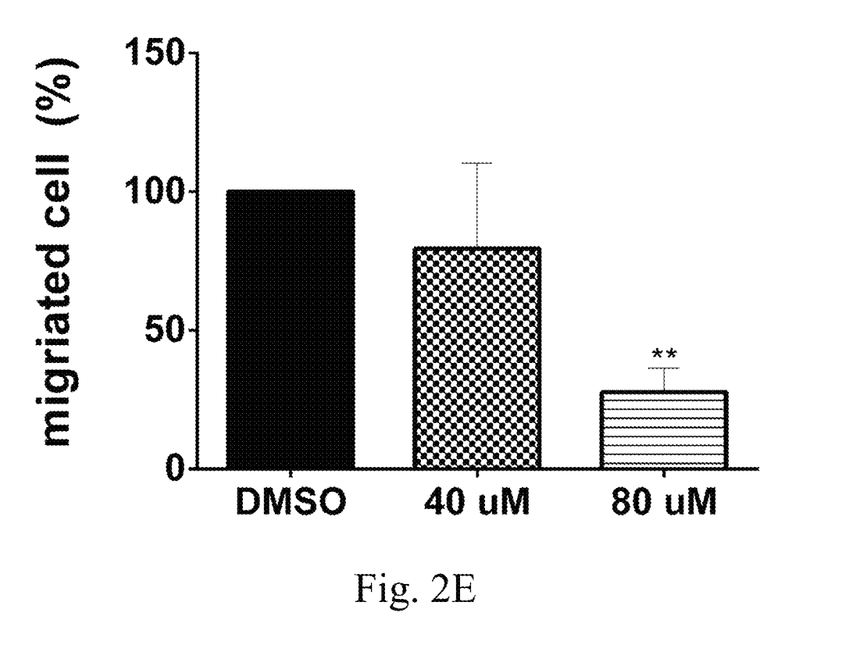

The data of colony formation assay demonstrated that the treatment of trilostane decreased colony numbers of Mahlavu and Hep3B cells (FIGS. 2A and 2B). The data of wound healing assay indicated that trilostane significantly inhibited the wound closure both in Mahlavu and Hep3B cells (FIGS. 2C and 2D). The inhibitory effect of trilostane on cell migration was further demonstrated by transwell migration assay (FIG. 2E).

These data indicated that HSD3B1 promotes the proliferation and migration of HCC cells in vitro, and the treatment of trilostane inhibits both the proliferation and migration ability of HCC cells.

Example 3 MEKK1/ERK Pathway Mediates the Effect of HSD3B1 Inhibition

Figure 3:
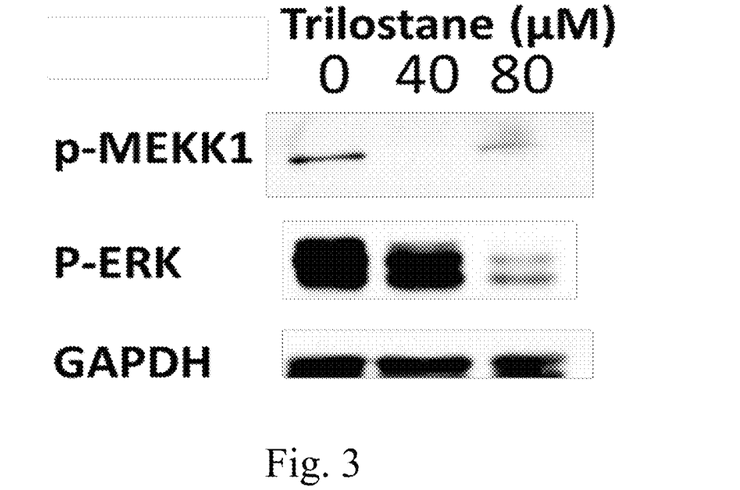
FIG. 3 is the data of western blot analysis that depicts the expression of phosphorylated MEKK1 (p-MEKK1) and phosphorylated ERK (p-ERK) in mahlave cells treated with specified concentration of trilostane according to Example 3 of the present disclosure.

In this example, RNA array was performed to investigate the molecular mechanism of HSD3B1 in regulating cell proliferation and migration. The result revealed that HSD3B1 inhibition attenuated the activity of the MEKK/ERK pathway (data not shown). That data of western blot analysis further confirmed that phosphorylated MEKK1 (p-MEKK1) and phosphorylated ERK (p-ERK) were down-regulated after trilostane treatment (FIG. 3).

Example 4 Trilostane Suppresses Tumor Growth In Vivo

Figure 4:
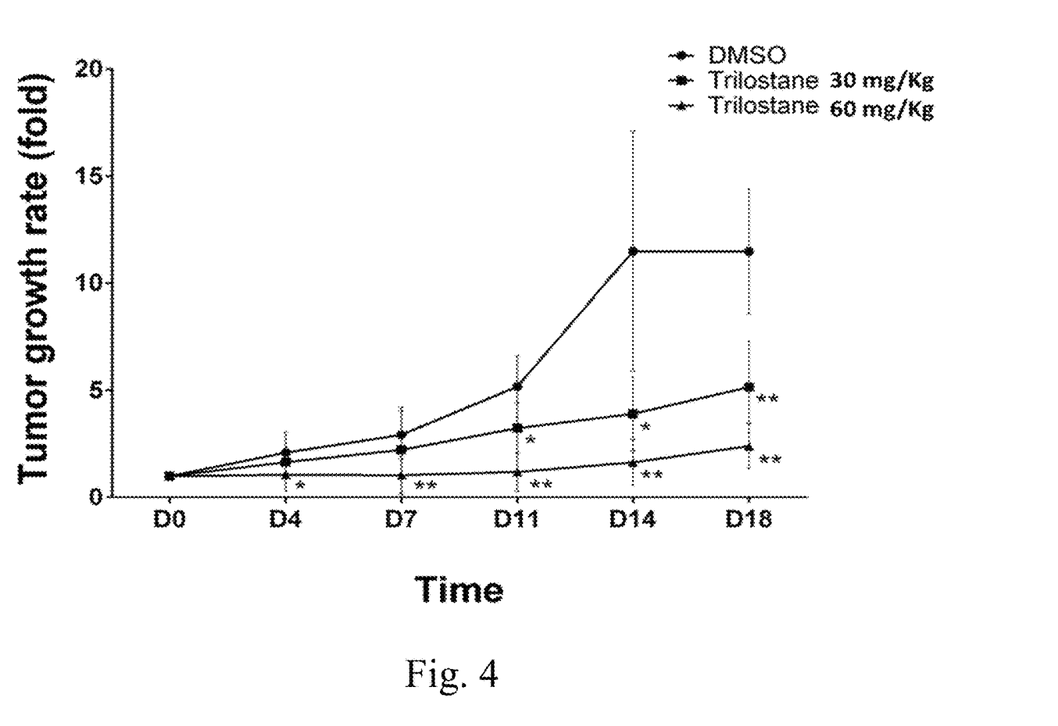
FIG. 4 is a line chart that depicts the inhibitory effect of trilostane on tumor growth in the subject according to Example 4 of the present disclosure

To validate the observations obtained from in vitro studies, a HCC xenograft mouse model was used to evaluate the relevance of HSD3B1 inhibition and tumor growth. Consistent with in vitro results, tumor growth rate was significantly suppressed by the treatment of trilostane (FIG. 4).

In conclusion, the present disclosure provides a novel biomarker for making a diagnosis of HCC. According to examples of the present disclosure, HSD3B1 is overexpressed in HCC, and is associated with the cell proliferation and migration. Accordingly, the present disclosure also provides a method of treating HCC by administering to a subject in need thereof an effective amount of HSD3B1 inhibitor (e.g., trilostane) so as to inhibit the tumor growth and/or alleviate/ameliorate the symptoms associated with HCC.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of treating hepatocellular carcinoma (HCC) in a subject, comprising administering to the subject an effective amount of an inhibitor of 3-beta-hydroxysteroid dehydrogenase type 1 (HSD3B1) selected from the group consisting of trilostane, epostane, and cyanoketone; wherein the mRNA or protein level of HSD3B1 in the HCC tumor tissue of the subject is higher than that in the non-tumor liver tissue of the subject.

2. The method of claim 1, wherein the inhibitor is trilostane.

3. The method of claim 1, wherein the effective amount is about 0.01-100 mg/kg body weight per day.

4. The method of claim 3, wherein the effective amount is about 0.1-10 mg/kg body weight per day.

5. The method of claim 4, wherein the effective amount is about 1-5 mg/kg body weight per day.

6. The method of claim 3, wherein the subject is a human.

7. A method of treating hepatocellular carcinoma (HCC) in a subject, comprising,
   (a) obtaining an HCC tumor tissue and a non-tumor liver tissue from the subject;
   (b) respectively measuring the mRNA or protein levels of HSD3B1 in the HCC tumor tissue and the non-tumor liver tissue; and
   (c) administering to the subject an effective amount of an inhibitor of 3-beta-hydroxysteroid dehydrogenase type 1 (HSD3B1) selected from the group consisting of trilostane, epostane, and cyanoketone; wherein the mRNA or protein level of HSD3B1 in the HCC tumor tissue is higher than that in the non-tumor liver tissue.

8. The method of claim 7, wherein the inhibitor is trilostane.

9. The method of claim 7, wherein the effective amount is about 0.01-100 mg/kg body weight per day.

10. The method of claim 9, wherein the effective amount is about 0.1-10 mg/kg body weight per day.

11. The method of claim 10, wherein the effective amount is about 1-5 mg/kg body weight per day.

12. The method of claim 7, wherein the subject is a human.

\* \* \* \* \*